United States Patent
Hsu

(10) Patent No.: US 8,297,290 B2
(45) Date of Patent: Oct. 30, 2012

(54) MULTI-ANGLED DENTAL FLOSS HOLDER

(75) Inventor: Walter W. Hsu, Dou Liu (TW)

(73) Assignee: Welter's Co., Ltd., Dou Liu, Yun Lin Hsien (TW)

( * ) Notice: Subject to any disclaimer, the term of this patent is extended or adjusted under 35 U.S.C. 154(b) by 448 days.

(21) Appl. No.: 12/568,881

(22) Filed: Sep. 29, 2009

(65) Prior Publication Data

US 2011/0073131 A1    Mar. 31, 2011

(51) Int. Cl.
*A61C 15/00* (2006.01)
(52) U.S. Cl. .................................. 132/323; 132/321
(58) Field of Classification Search ........... 132/321–329
See application file for complete search history.

(56) References Cited

U.S. PATENT DOCUMENTS

| | | | | |
|---|---|---|---|---|
| 1,989,895 A * | 2/1935 | Van Gilder | .................... | 132/323 |
| 2,837,098 A * | 6/1958 | Sorboro | ........................ | 132/324 |
| 3,927,686 A * | 12/1975 | Zambito | ........................ | 132/323 |
| 4,304,246 A * | 12/1981 | Yafai | .............................. | 132/323 |
| 5,063,948 A * | 11/1991 | Lloyd | ........................... | 132/321 |
| 6,082,999 A * | 7/2000 | Tcherny et al. | .................. | 433/80 |
| 2006/0266378 A1 * | 11/2006 | Liu et al. | ........................ | 132/325 |
| 2007/0044815 A1 * | 3/2007 | Ashraf | ........................... | 132/323 |
| 2008/0047574 A1 * | 2/2008 | Yim | .............................. | 132/323 |
| 2008/0163888 A1 * | 7/2008 | Chen | ............................. | 132/323 |

* cited by examiner

*Primary Examiner* — Todd Manahan
*Assistant Examiner* — Brianne Kalach
(74) *Attorney, Agent, or Firm* — Alan Kamrath; Kamrath IP Lawfirm, PA

(57) ABSTRACT

A dental floss holder includes a shank (11), an adjusting member (12) pivotally mounted on the shank and a cleaning unit (20) detachably mounted on the adjusting member. Thus, the rotation portion (111) of the shank is rotated relative to the mounting portion (122) of the adjusting member to adjust the inclined angle between the shank and the adjusting member so that the inclined angle between the shank and the cleaning unit is adjusted according to a user's requirement so as to facilitate the user clearing the teeth in different inclined angles.

16 Claims, 10 Drawing Sheets

MULTI-ANGLED DENTAL FLOSS HOLDER

BACKGROUND OF THE INVENTION

1. Field of the Invention

The present invention relates to a dental floss holder and, more particularly, to a multi-angled dental floss holder.

2. Description of the Related Art

A first conventional dental floss holder in accordance with the prior art shown in FIG. 13 comprises a substantially Y-shaped support bar 30 and a linear dental floss 31 secured on the upper end of the support bar 30. However, the dental floss 31 and the support bar 30 are combined integrally so that when the dental floss 31 is used up or worn out, the dental floss 31 together with the support bar 30 has to be thrown away or disposed of, thereby increasing the cost of material. In addition, the dental floss 31 is secured on the support bar 30 so that the angle of the dental floss 31 cannot be adjusted according to a user's requirement, thereby causing inconvenience to the user when clearing the teeth.

A second conventional dental floss holder in accordance with the prior art shown in FIG. 14 comprises a substantially F-shaped support bar 32 and a linear dental floss 33 secured on the upper end of the support bar 32. However, the dental floss 33 and the support bar 32 are combined integrally so that when the dental floss 33 is used up or worn out, the dental floss 33 together with the support bar 32 has to be thrown away or disposed of, thereby increasing the cost of material. In addition, the dental floss 33 is secured on the support bar 32 so that the angle of the dental floss 33 cannot be adjusted according to a user's requirement, thereby causing inconvenience to the user when clearing the teeth.

BRIEF SUMMARY OF THE INVENTION

In accordance with the present invention, there is provided a dental floss holder, comprising a shank, an adjusting member pivotally mounted on the shank and a cleaning unit detachably mounted on the adjusting member.

According to the primary objective of the present invention, the rotation portion of the shank is rotated relative to the mounting portion of the adjusting member to adjust the inclined angle between the shank and the adjusting member so that the inclined angle between the shank and the cleaning unit is adjusted according to a user's requirement so as to facilitate the user clearing the teeth in different inclined angles.

According to another objective of the present invention, the adjusting member can be detached from the shank, and the cleaning unit can be detached from the adjusting member so that the cleaning unit and the adjusting member can be replaced individually, thereby saving the cost of material.

According to a further objective of the present invention, the cleaning unit includes a first clearing portion to scrape and remove the food residuals between the user's any two adjacent teeth, and at least two second clearing portions to rub and clear the peripheral corner of each of the user's teeth, thereby enhancing the cleaning effect.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

DETAILED DESCRIPTION OF THE INVENTION

Figure 1:
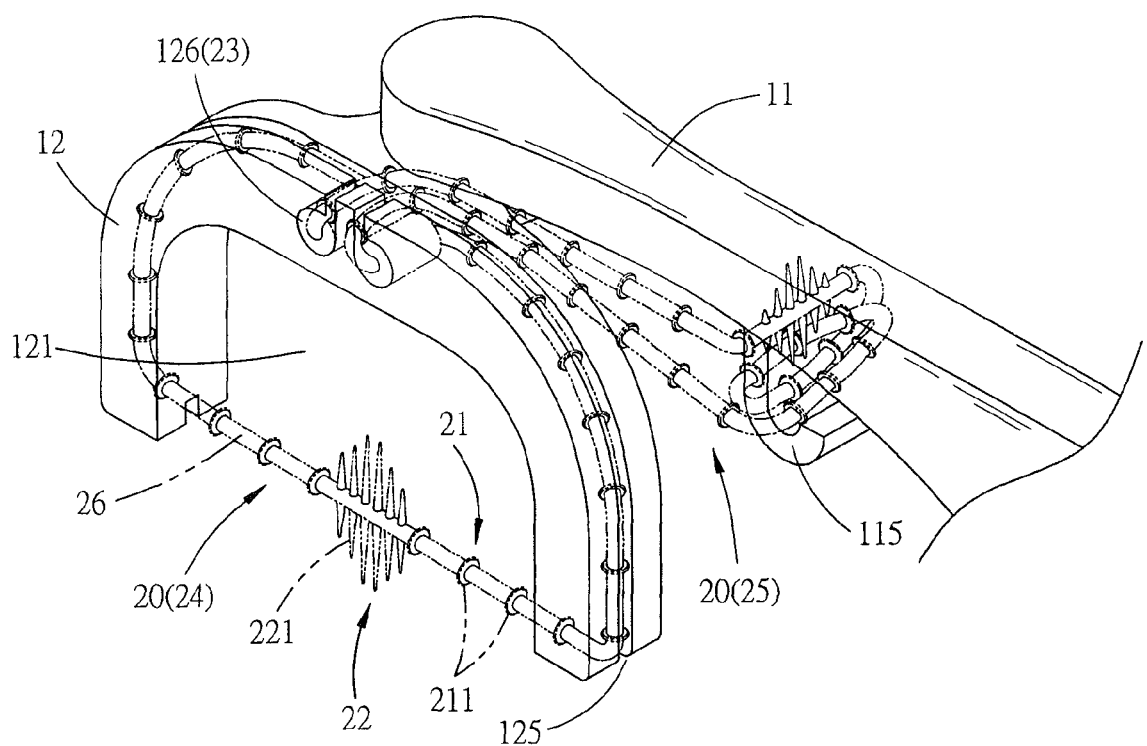
FIG. 1 is a perspective view of a dental floss holder in accordance with the preferred embodiment of the present invention.
Figure 2:
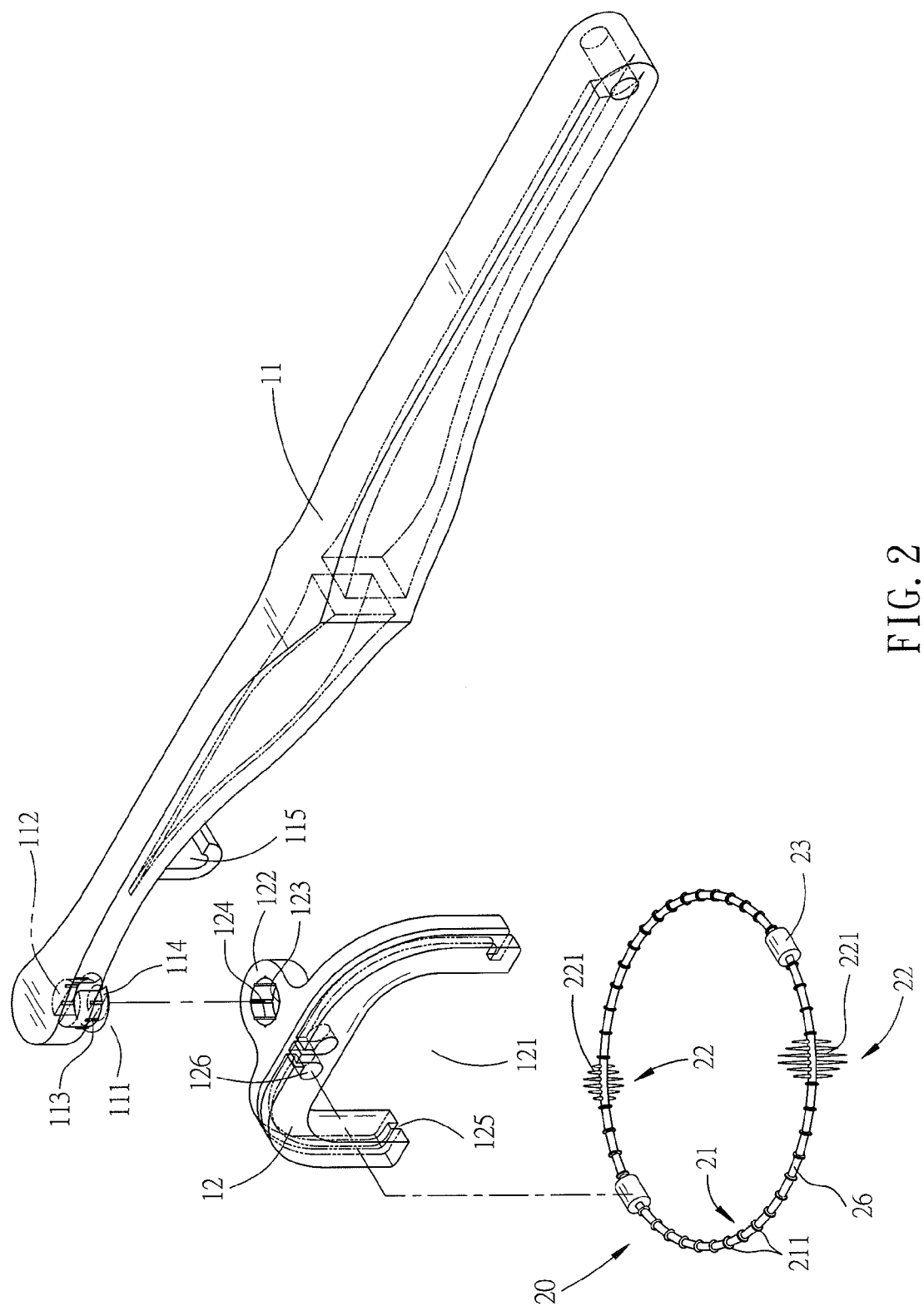
FIG. 2 is an exploded perspective view of the dental floss holder as shown in FIG. 1.
Figure 3:
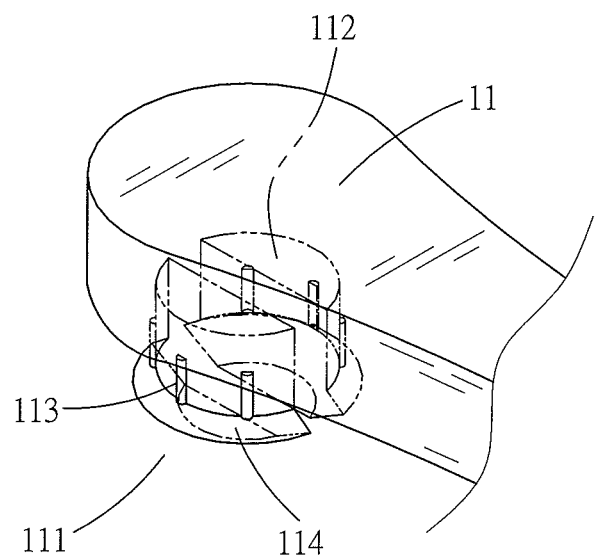
FIG. 3 is a perspective view of a shank of the dental floss holder as shown in FIG. 1.
Figure 4:
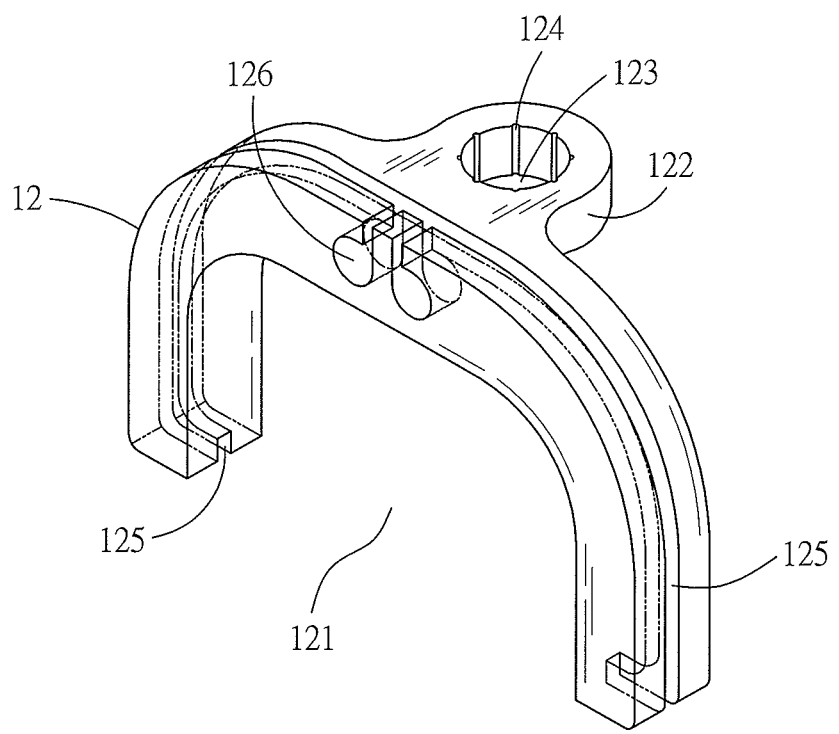
FIG. 4 is a perspective view of an adjusting member of the dental floss holder as shown in FIG. 1.
Figure 5:
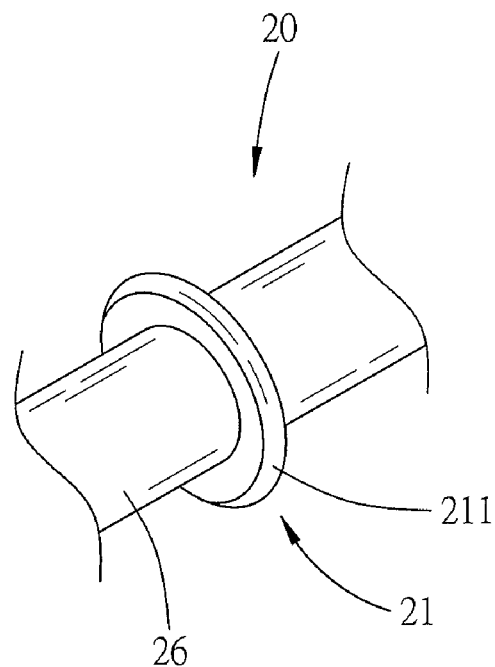
FIG. 5 is a perspective view of a cleaning unit of the dental floss holder as shown in FIG. 1.
Figure 6:
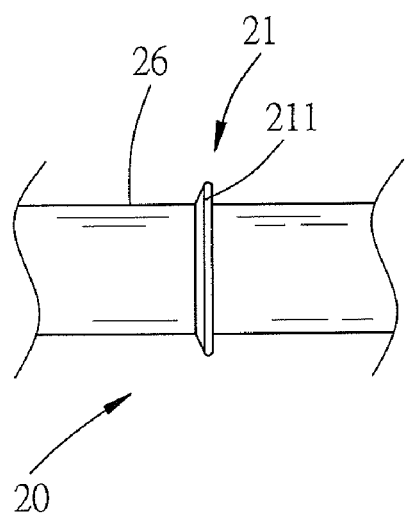
FIG. 6 is a front view of the cleaning unit of the dental floss holder as shown in FIG. 5.

Referring to the drawings and initially to FIGS. 1-7, a dental floss holder in accordance with the preferred embodiment of the present invention comprises a shank 11, an adjusting member 12 pivotally mounted on the shank 11, and a cleaning unit 20 detachably mounted on the adjusting member 12.

The adjusting member 12 has a side provided with a protruding mounting portion 122. The mounting portion 122 of the adjusting member 12 has an inside provided with a pivot hole 123. The pivot hole 123 of the mounting portion 122 has a substantially circular shape and has a peripheral wall provided with a plurality of adjusting channels 124. The adjusting member 12 has a substantially inverted U-shaped profile and has an inside provided with an operation space 121 to allow passage of the cleaning unit 20. The adjusting member 12 has a peripheral wall provided with a mounting slot 125 which has a substantially inverted U-shaped profile. The mounting slot 125 of the adjusting member 12 has two opposite ends each connected to the operation space 121. The adjusting member 12 has a mediate portion provided with two retaining grooves 126 each connected to the mounting slot 125. Each of the two retaining grooves 126 of the adjusting member 12 has a substantially C-shaped profile.

The shank 11 has a side provided with a hook-shaped receiving portion 115. The shank 11 has an end provided with a rotation portion 111 rotatably mounted on the mounting portion 122 of the adjusting member 12. The rotation portion 111 of the shank 11 is detachably mounted on the mounting portion 122 of the adjusting member 12 and includes two elastic pieces 112 each rotatably mounted in the pivot hole 123 of the mounting portion 122. The two elastic pieces 112 of the rotation portion 111 are spaced from each other and are arranged radially opposite to each other. Each of the two elastic pieces 112 of the rotation portion 111 has a substantially semi-circular shape and has a peripheral wall provided with a plurality of adjusting ribs 113 detachably locked in the adjusting channels 124 of the mounting portion 122. Each of the two elastic pieces 112 of the rotation portion 111 has a lower end provided with a protruding stop flange 114 protruding outwardly from the pivot hole 123 of the mounting portion 122 and abutting a bottom of the mounting portion 122 of the adjusting member 12 to prevent the rotation portion 111 of the shank 11 from being detached from the mounting portion 122 of the adjusting member 12.

The cleaning unit 20 includes a cleaning body 26 detachably mounted on the adjusting member 12, a first clearing portion 21 mounted on the cleaning body 26, and at least two second clearing portions 22 mounted on the cleaning body 26. The cleaning body 26 of the cleaning unit 20 has a ring shape or a linear shape. The cleaning body 26 of the cleaning unit 20 is partially received in the mounting slot 125 and the operation space 121 of the adjusting member 12 and partially received in the receiving portion 115 of the shank 11. The cleaning body 26 of the cleaning unit 20 extends into the operation space 121 of the adjusting member 12. The cleaning body 26 of the cleaning unit 20 is mounted on the mounting slot 125 of the adjusting member 12 from the two opposite ends of the mounting slot 125 and extends through a whole length of the mounting slot 125. The first clearing portion 21 of the cleaning unit 20 consists of a plurality of scraping pieces 211. The first clearing portion 21 of the cleaning unit 20 is partially received in the operation space 121 of the adjusting member 12. Each of scraping pieces 211 of the first clearing portion 21 has an annular chamfered shape. The second clearing portions 22 of the cleaning unit 20 are partially received in the operation space 121 of the adjusting member 12. Each of the second clearing portions 22 of the cleaning unit 20 consists of a plurality of soft upright rubbing strips 221. The rubbing strips 221 of each of the second clearing portions 22 have different lengths.

The cleaning unit 20 further includes two locking points 23 mounted on the cleaning body 26. The two locking points 23 of the cleaning unit 20 are detachably locked in the two retaining grooves 126 of the adjusting member 12 respectively. The cleaning body 26 of the cleaning unit 20 is divided by the two locking points 23 into a first operation section 24 and a second operation section 25 as shown in FIG. 1. The first operation section 24 of the cleaning body 26 extends through the mounting slot 125 of the adjusting member 12 and extends into the operation space 121 of the adjusting member 12. The first clearing portion 21 and one of the second clearing portions 22 on the first operation section 24 of the cleaning body 26 are located in and exposed from the operation space 121 of the adjusting member 12. The second operation section 25 of the cleaning body 26 is stored by the receiving portion 115 of the shank 11.

Figure 7:
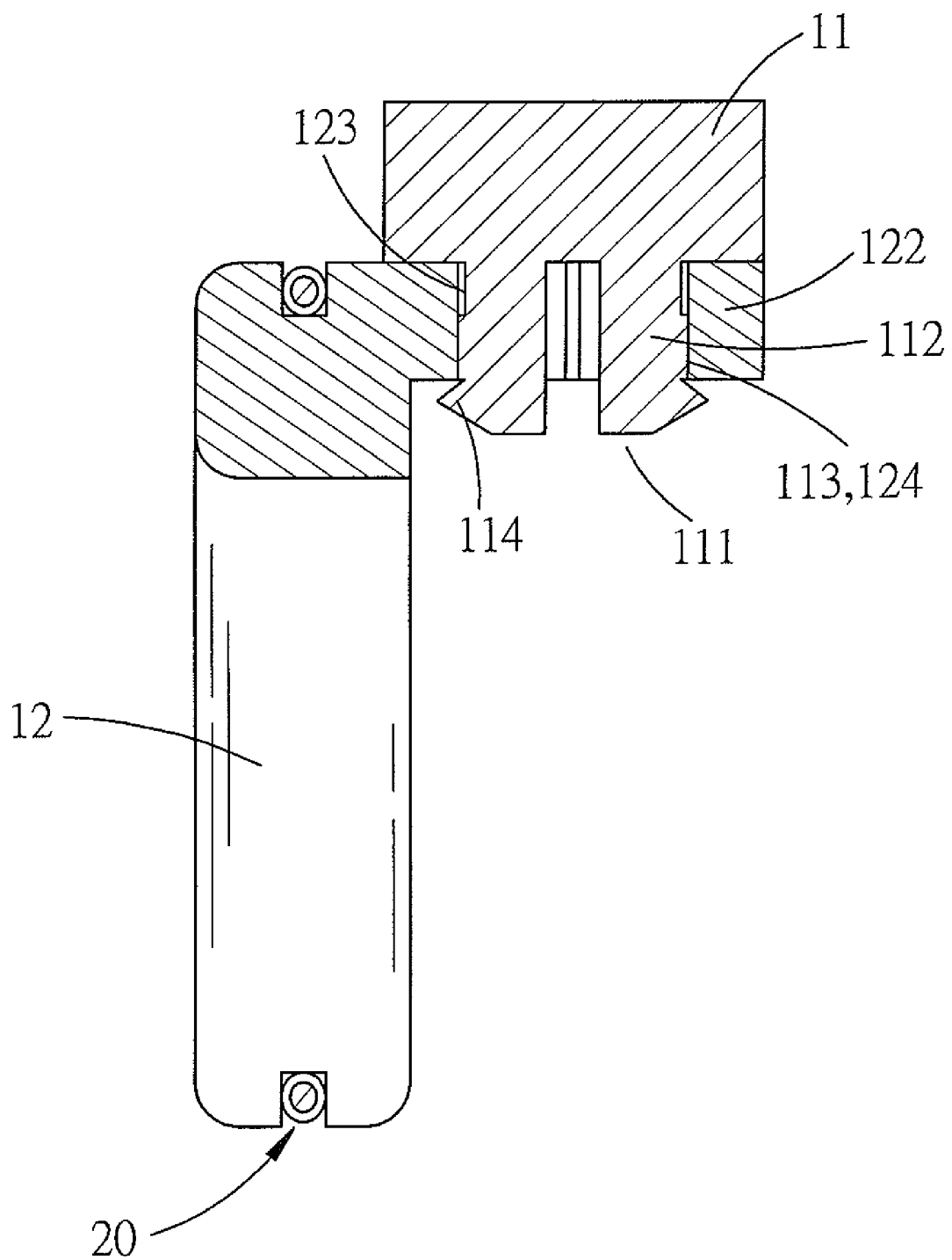
FIG. 7 is a side cross-sectional view of the dental floss holder as shown in FIG. 1.

In assembly, again referring to FIGS. 1-7, when the adjusting member 12 is mounted on the shank 11, the two elastic pieces 112 of the rotation portion 111 are inserted into the pivot hole 123 of the mounting portion 122. At this time, each of the two elastic pieces 112 of the rotation portion 111 has a lower end provided with a protruding stop flange 114 protruding outwardly from the pivot hole 123 of the mounting portion 122 and abutting the bottom of the mounting portion 122 of the adjusting member 12 as shown in FIG. 7 to prevent the rotation portion 111 of the shank 11 from being detached from the mounting portion 122 of the adjusting member 12. Then, the cleaning body 26 of the cleaning unit 20 extends through the operation space 121 of the adjusting member 12. Then, the cleaning body 26 of the cleaning unit 20 is mounted on the mounting slot 125 of the adjusting member 12 from the two opposite ends of the mounting slot 125 and extends through a whole length of the mounting slot 125. Then, the two locking points 23 of the cleaning unit 20 are insert into and locked in the two retaining grooves 126 of the adjusting member 12 respectively. Then, the cleaning body 26 of the cleaning unit 20 is extended outwardly from the adjusting member 12 and received in the receiving portion 115 of the shank 11. Thus, the cleaning body 26 of the cleaning unit 20 is partially received in the mounting slot 125 and the operation space 121 of the adjusting member 12 and partially received in the receiving portion 115 of the shank 11, so that the first operation section 24 of the cleaning body 26 extends through the mounting slot 125 of the adjusting member 12 and extends into the operation space 121 of the adjusting member 12 for operation of a user, while the second operation section 25 of the cleaning body 26 is stored by the receiving portion 115 of the shank 11 as shown in FIG. 1 for the next use. At this time, the first clearing portion 21 and the second clearing portion 22 on the first operation section 24 of the cleaning body 26 are located in and exposed from the operation space 121 of the adjusting member 12.

In operation, referring to FIGS. 1-8, when the cleaning body 26 of the cleaning unit 20 is inserted and moved between a user's two teeth, the scraping pieces 211 of the first clearing portion 21 on the first operation section 24 of the cleaning body 26 can be used to scrape and remove the food residuals between the user's any two adjacent teeth, and the soft rubbing strips 221 of the second clearing portion 22 on the first operation section 24 of the cleaning body 26 can be used to rub and clear the peripheral corner of each of the user's teeth.

Figure 8:
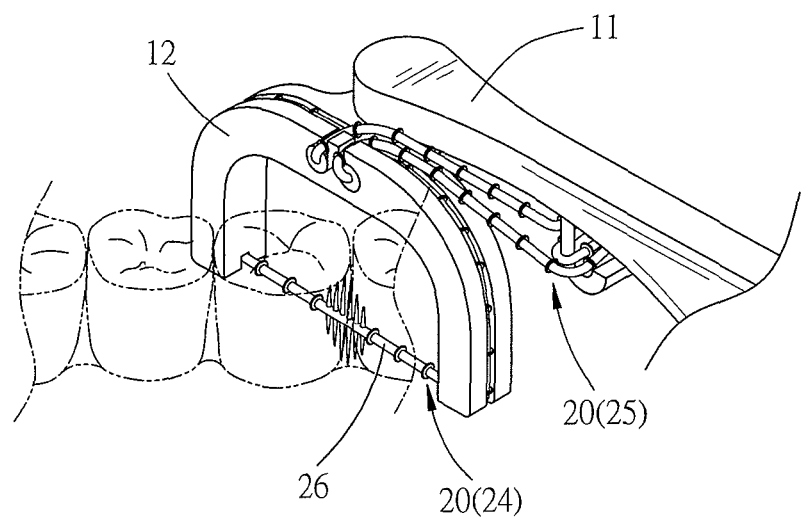
FIG. 8 is a schematic operational view of the dental floss holder as shown in FIG. 1.
Figure 9:
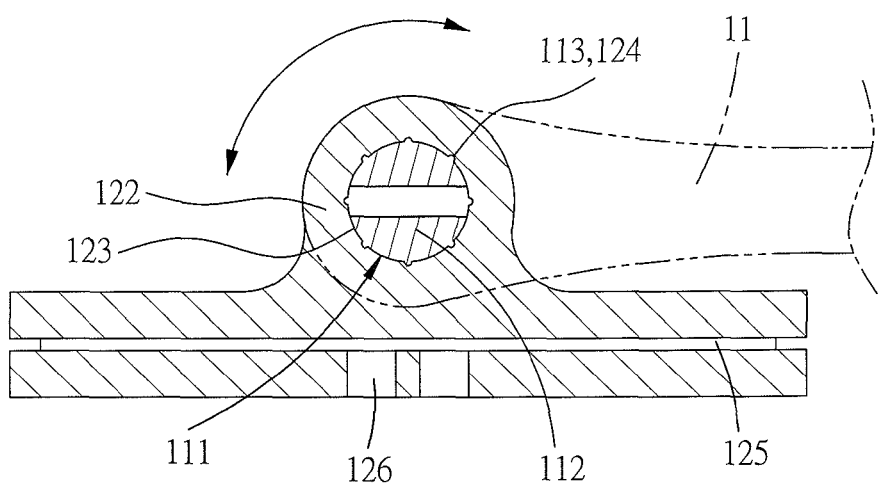
FIG. 9 is a top cross-sectional operational view of the dental floss holder as shown in FIG. 8.

As shown in FIGS. 8 and 9, when the shank 11 is rotated relative to the adjusting member 12, the rotation portion 111 of the shank 11 is rotated relative to the mounting portion 122 of the adjusting member 12 to adjust the inclined angle between the shank 11 and the adjusting member 12 so as to facilitate the user clearing the teeth in different inclined angles. At this time, the adjusting ribs 113 of each of the two elastic pieces 112 are locked in the adjusting channels 124 of the mounting portion 122 to lock the rotation portion 111 of the shank 11 onto the mounting portion 122 of the adjusting member 12.

Figure 10:
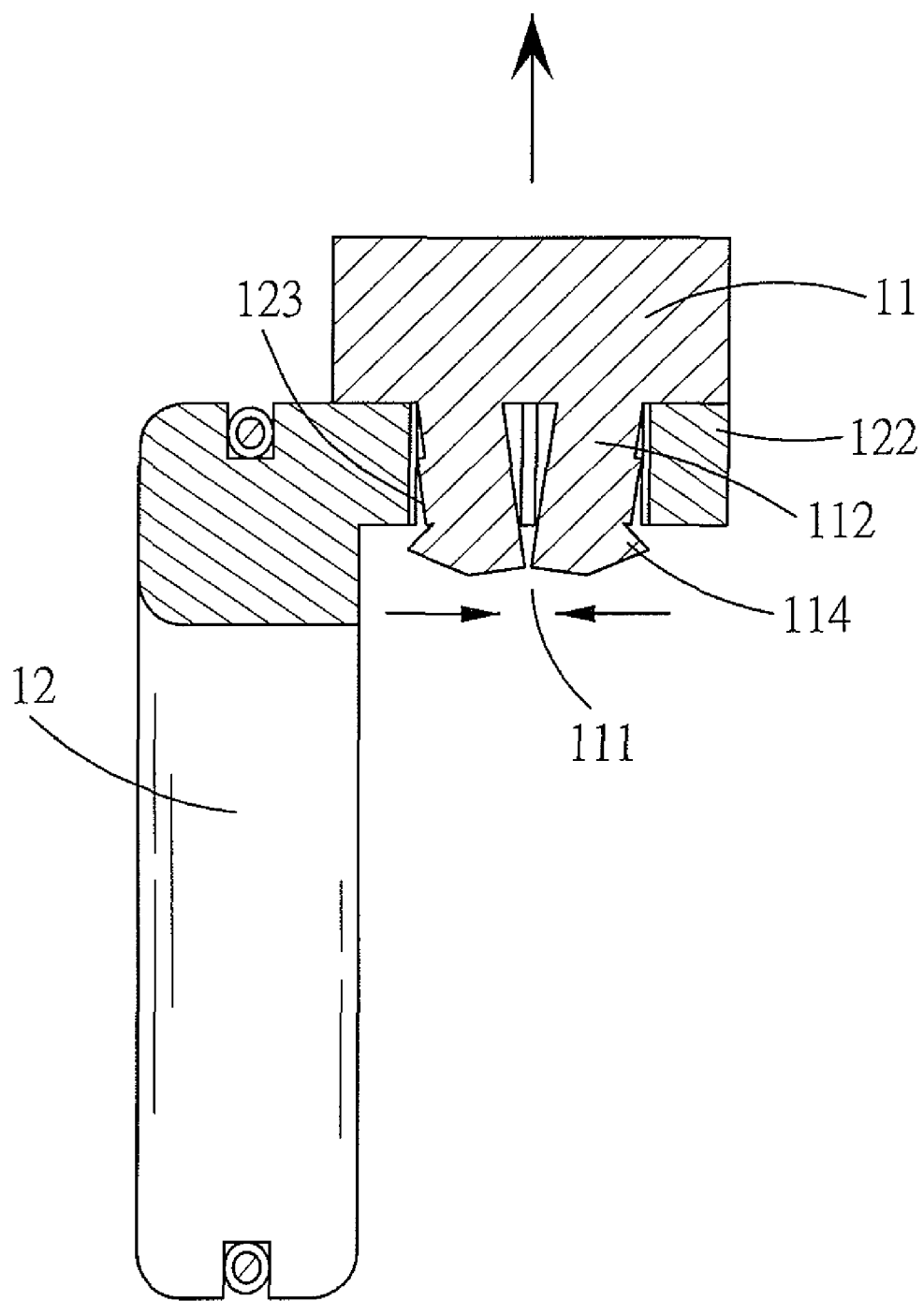
FIG. 10 is a schematic operational view of the dental floss holder as shown in FIG. 7.

As shown in FIG. 10, when the two elastic pieces 112 of the rotation portion 111 are pressed toward each other, the stop flange 114 of each of the two elastic pieces 112 is detached from the bottom of the mounting portion 122 of the adjusting member 12, so that the rotation portion 111 of the shank 11 is unlocked from the mounting portion 122 of the adjusting member 12 and can be detached from the pivot hole 123 of the mounting portion 122 to remove the adjusting member 12 from the shank 11 for replacement of the adjusting member 12.

Figure 11:
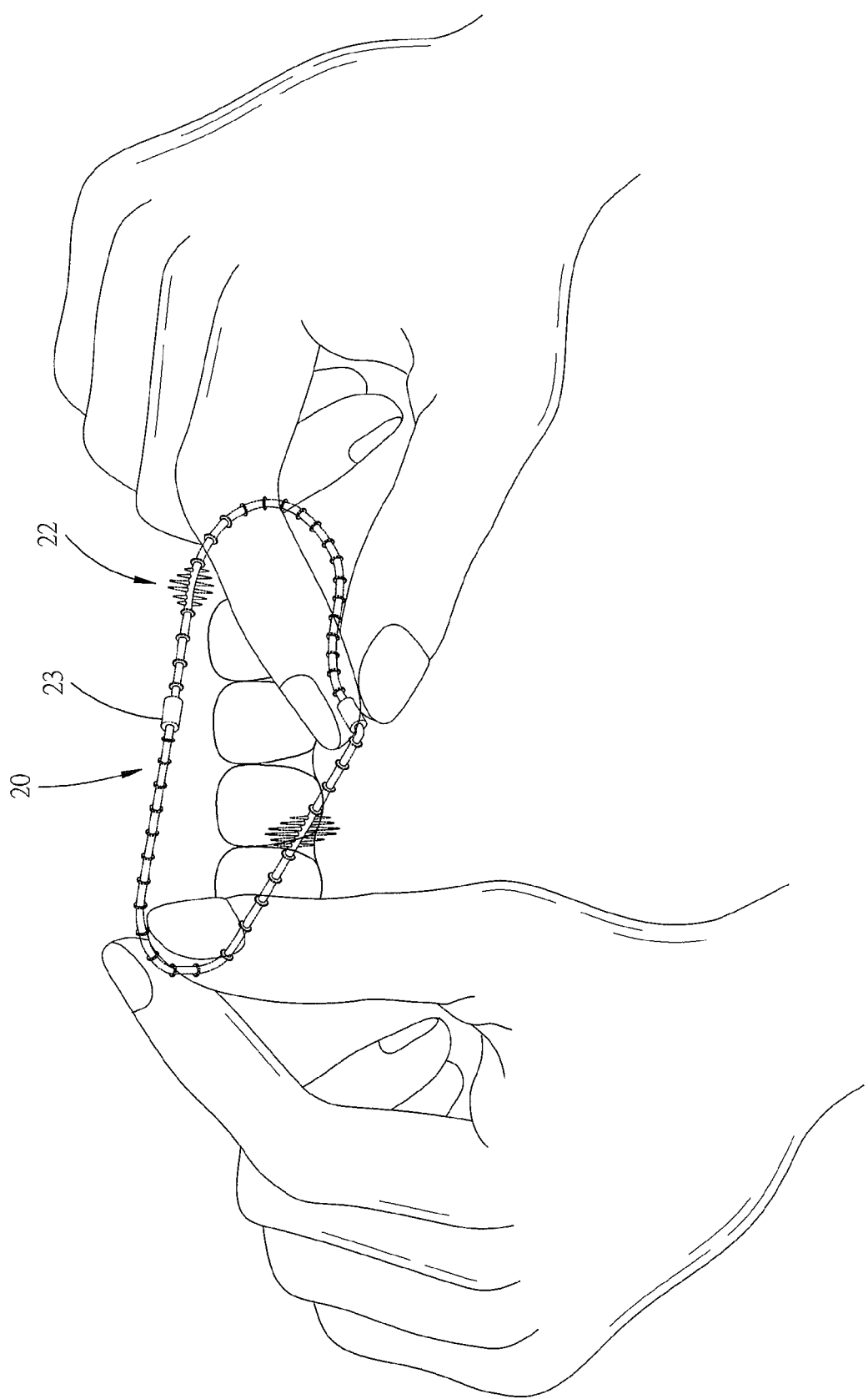
FIG. 11 is a schematic operational view of the cleaning unit of the dental floss holder as shown in FIG. 1.

As shown in FIG. 11, the cleaning unit 20 is used individually.

Figure 12:
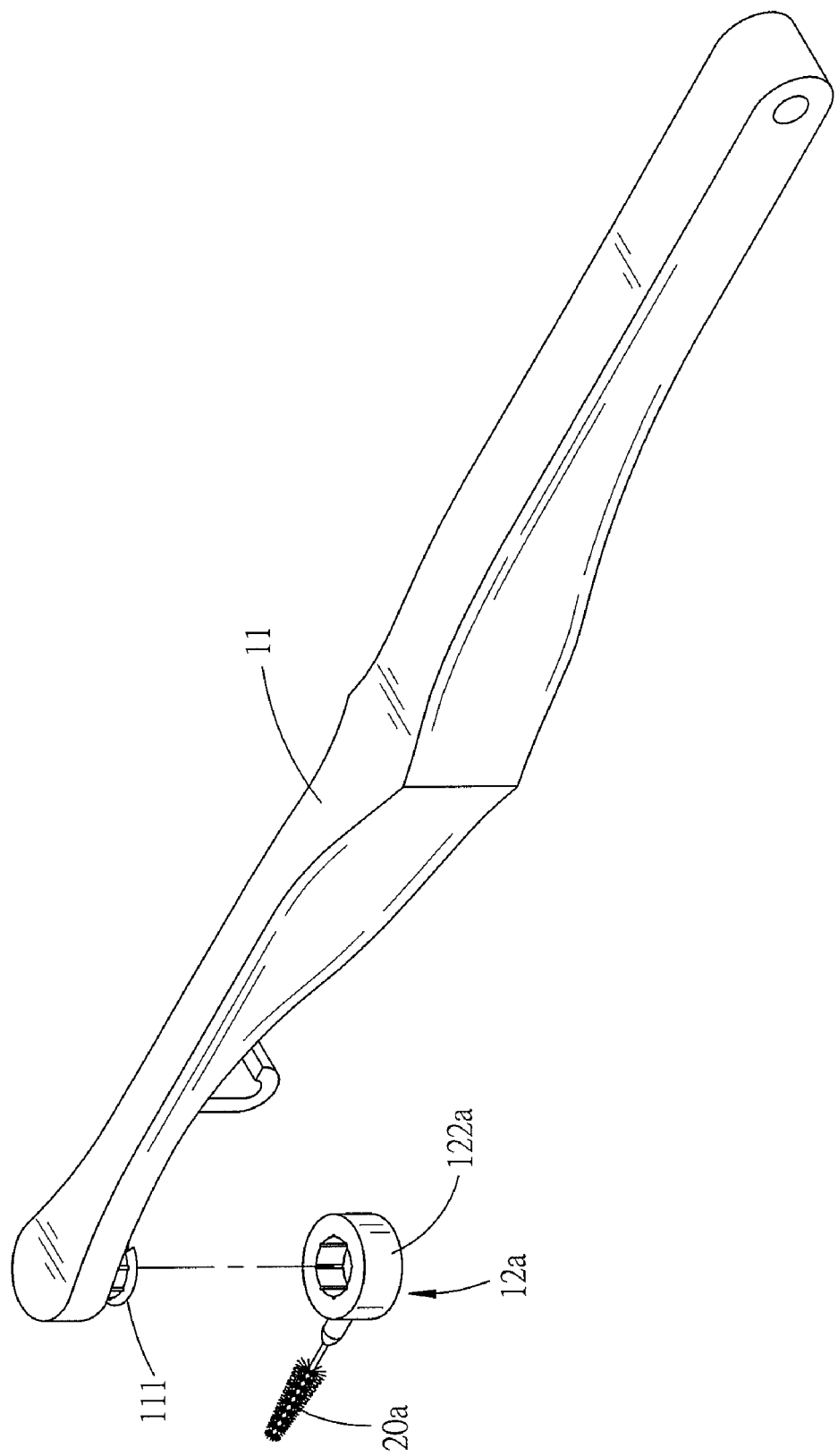
FIG. 12 is an exploded perspective view of a dental floss holder in accordance with another preferred embodiment of the present invention.
Figure 13:
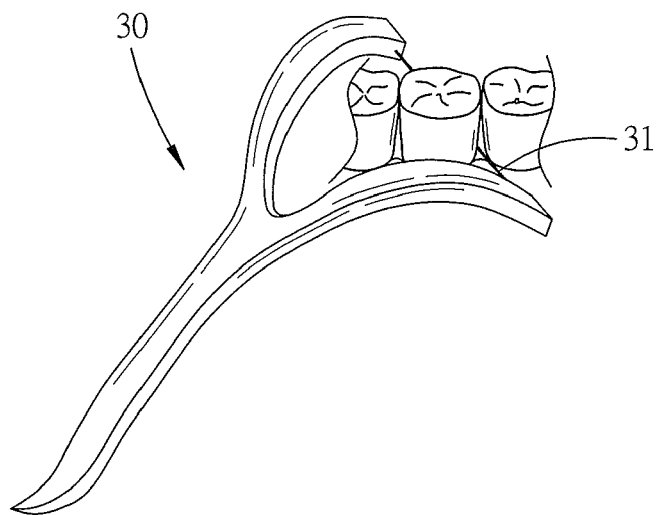
FIG. 13 is a perspective view of a first conventional dental floss holder in accordance with the prior art.
Figure 14:
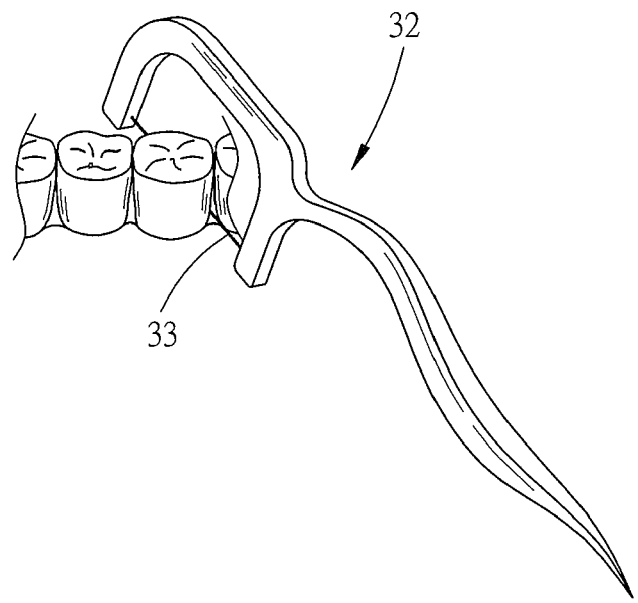
FIG. 14 is a perspective view of a first conventional dental floss holder in accordance with the prior art.

As shown in FIG. 12, the mounting portion 122a of the adjusting member 12a has a circular shape, and the cleaning unit 20a is an interdental brush.

Accordingly, the rotation portion 111 of the shank 11 is rotated relative to the mounting portion 122 of the adjusting member 12 to adjust the inclined angle between the shank 11 and the adjusting member 12 so that the inclined angle between the shank 11 and the cleaning unit 20 is adjusted according to a user's requirement so as to facilitate the user clearing the teeth in different inclined angles. In addition, the adjusting member 12 can be detached from the shank 11, and the cleaning unit 20 can be detached from the adjusting member 12 so that the cleaning unit 20 and the adjusting member 12 can be replaced individually, thereby saving the cost of material. Further, the cleaning unit 20 includes a first clearing portion 21 to scrape and remove the food residuals between the user's any two adjacent teeth, and at least two second clearing portions 22 to rub and clear the peripheral corner of each of the user's teeth, thereby enhancing the cleaning effect.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

The invention claimed is:

1. A dental floss holder, comprising:
a shank (11);
an adjusting member (12) pivotally mounted on the shank;
a cleaning unit (20) detachably mounted on the adjusting member;
wherein the adjusting member has a side provided with a protruding mounting portion (122);
the shank has an end provided with a rotation portion (111) rotatably mounted on the mounting portion of the adjusting member;
the cleaning unit includes:
a cleaning body 26 detachably mounted on the adjusting member;
a first clearing portion (21) mounted on the cleaning body;
at least two second clearing portions (22) mounted on the cleaning body;
the first clearing portion of the cleaning unit consists of a plurality of scraping pieces (211);
each of the second clearing portions of the cleaning unit has a form different from that of the first clearing portion;
each of the second clearing portions of the cleaning unit consists of a plurality of soft upright rubbing strips (221);
each of scraping pieces of the first clearing portion has an annular chamfered shape;
wherein the shank has a side provided with a hook-shaped receiving portion; the cleaning body of the cleaning unit is partially received in the adjusting member and partially received in the receiving portion of the shank; the first clearing portion of the cleaning unit is partially received in the adjusting member; the second clearing portions of the cleaning unit are partially received in the adjusting member.

2. The dental floss holder of claim 1, wherein
the mounting portion of the adjusting member has an inside provided with a pivot hole (123);
the rotation portion of the shank includes two elastic pieces (112) each rotatably mounted in the pivot hole of the mounting portion;
the two elastic pieces of the rotation portion are spaced from each other and are arranged radially opposite to each other;
each of the two elastic pieces of the rotation portion has a lower end provided with a protruding stop flange (114) protruding outwardly from the pivot hole of the mounting portion and abutting a bottom of the mounting portion of the adjusting member to prevent the rotation portion of the shank from being detached from the mounting portion of the adjusting member.

3. The dental floss holder of claim 2, wherein
the pivot hole of the mounting portion has a peripheral wall provided with a plurality of adjusting channels (124);
each the adjusting channels of the mounting portion extends in a longitudinal direction of the mounting portion;
each of the two elastic pieces of the rotation portion has a peripheral wall provided with a plurality of adjusting ribs (113) detachably locked in the adjusting channels of the mounting portion;

each the adjusting ribs of each of the two elastic pieces extends in a longitudinal direction of the rotation portion.

4. The dental floss holder of claim 1, wherein the adjusting member has a substantially inverted U-shaped profile and has an inside provided with an operation space (121) to allow passage of the cleaning unit.

5. The dental floss holder of claim 4, wherein
the adjusting member has a peripheral wall provided with a mounting slot (125) which has a substantially inverted U-shaped profile;
the adjusting member has a mediate portion provided with two retaining grooves (126) each connected to the mounting slot;
each of the two retaining grooves of the adjusting member has a substantially C-shaped profile;
the cleaning unit further includes two locking points (23) mounted on the cleaning body;
the two locking points of the cleaning unit are detachably locked in the two retaining grooves of the adjusting member respectively.

6. The dental floss holder of claim 1, wherein the shank has a side provided with a hook-shaped receiving portion (115) to receive the cleaning unit partially.

7. The dental floss holder of claim 1, wherein the cleaning body of the cleaning unit has a ring shape or a linear shape.

8. The dental floss holder of claim 1, wherein the cleaning unit is an interdental brush.

9. The dental floss holder of claim 1, wherein the rubbing strips of each of the second clearing portions have different lengths.

10. The dental floss holder of claim 2, wherein
the pivot hole of the mounting portion has a substantially circular shape;
each of the two elastic pieces of the rotation portion has a substantially semi-circular shape.

11. The dental floss holder of claim 5, wherein the mounting slot of the adjusting member has two opposite ends each connected to the operation space.

12. The dental floss holder of claim 5, wherein
the cleaning body of the cleaning unit is divided by the two locking points into a first operation section and a second operation section;
the first operation section of the cleaning body extends through the mounting slot of the adjusting member and extends into the operation space of the adjusting member;
the first clearing portion and one of the second clearing portions on the first operation section of the cleaning body are located in and exposed from the operation space of the adjusting member.

13. The dental floss holder of claim 1, wherein the rotation portion of the shank is detachably mounted on the mounting portion of the adjusting member.

14. The dental floss holder of claim 1, wherein the mounting portion of the adjusting member has a circular shape.

15. The dental floss holder of claim 5, wherein the cleaning body of the cleaning unit extends through a whole length of the mounting slot.

16. The dental floss holder of claim 11, wherein the cleaning body of the cleaning unit is mounted on the mounting slot of the adjusting member from the two opposite ends of the mounting slot.

* * * * *